US012656305B2

(12) United States Patent
Baehl

(10) Patent No.: US 12,656,305 B2
(45) Date of Patent: Jun. 16, 2026

(54) SYSTEMS AND METHODS FOR A TEST STRIP CALIBRATOR SIMULATING AN ELECTROCHEMICAL TEST STRIP

(71) Applicant: Polymer Technology Systems, Inc., Whitestown, IN (US)

(72) Inventor: Brian David Baehl, Fishers, IN (US)

(73) Assignee: Polymer Technology Systems, Inc., Whitestown, IN (US)

( * ) Notice: Subject to any disclaimer, the term of this patent is extended or adjusted under 35 U.S.C. 154(b) by 275 days.

(21) Appl. No.: 16/998,906

(22) Filed: Aug. 20, 2020

(65) Prior Publication Data

US 2022/0057358 A1     Feb. 24, 2022

(51) Int. Cl.
*G01N 27/416*     (2006.01)
*A61B 5/1468*     (2006.01)
*A61B 5/15*     (2006.01)

(52) U.S. Cl.
CPC ....... *G01N 27/4163* (2013.01); *A61B 5/1468* (2013.01); *A61B 5/150358* (2013.01); *A61B 2560/0223* (2013.01)

(58) Field of Classification Search
CPC ............ G01N 27/4163; G01N 27/3274; A61B 5/1468; A61B 5/150358; A61B 2560/0223
See application file for complete search history.

(56) References Cited

U.S. PATENT DOCUMENTS 4,714,874 A     12/1987     Morris et al.
5,124,661 A     6/1992     Zelin et al.

5,438,271 A     8/1995     White et al.
7,514,040 B2     4/2009     Wu et al.
2003/0204313 A1 *     10/2003     Ou-Yang .......... G01N 33/48771
                                                              702/19
2005/0023152 A1 *     2/2005     Surridge ............ G01N 27/3272
                                                              204/403.1
2009/0113981 A1     5/2009     Beer
2009/0119047 A1 *     5/2009     Zelin ........................ G01K 3/04
                                                              702/82
2013/0031772 A1     2/2013     Petyt et al.
(Continued)

FOREIGN PATENT DOCUMENTS

WO          200250528 A1     6/2002
WO     WO-2006119203 A2 *     11/2006     ............. B82Y 15/00
(Continued)

OTHER PUBLICATIONS

International Search Report and Written Opinion dated Dec. 1, 2021 issued in related PCT App. No. PCT/US 21/46764 (18 pages).
(Continued)

*Primary Examiner* — Shizhi Qian
(74) *Attorney, Agent, or Firm* — Haynes and Boone, LLP; Robert P. Ziemian

(57) ABSTRACT

A system for calibrating an analyzer includes a test strip body. The system further includes a plurality of leads on the test strip body. The system further includes a circuit on the test strip body. The circuit includes a first resistor interconnected with at least a first portion of the plurality of leads and a second resistor interconnected with at least a second portion of the plurality of leads. When the test strip body is inserted into an analyzer, the circuit is configured to provide a signal simulating an electrochemical test strip.

8 Claims, 3 Drawing Sheets

(56) References Cited

U.S. PATENT DOCUMENTS

| | | | |
|---|---|---|---|
| 2016/0033439 A1* | 2/2016 | Elder ................. | G01N 27/3273 |
| | | | 205/792 |
| 2016/0061763 A1* | 3/2016 | Iyengar ................... | A61B 5/05 |
| | | | 204/406 |
| 2017/0023516 A1* | 1/2017 | Hamer ............... | G01N 27/3273 |
| 2018/0172618 A1* | 6/2018 | Blythe ............... | G01N 27/3274 |

FOREIGN PATENT DOCUMENTS

| | | | | |
|---|---|---|---|---|
| WO | WO-2015097179 A1 * | 7/2015 | ......... | G01N 27/3273 |
| WO | WO-2018193017 A1 * | 10/2018 | ......... | A61B 5/14532 |

OTHER PUBLICATIONS

International Search Reported dated Jul. 18, 2024 in parallel European Patent Application No. 21859157.6 (7 pages).

* cited by examiner

SYSTEMS AND METHODS FOR A TEST STRIP CALIBRATOR SIMULATING AN ELECTROCHEMICAL TEST STRIP

BACKGROUND

Diagnostic testing devices find usage in many scenarios, including home use, use by a doctor's office, and usage at health fairs. Diagnostic testing devices typically perform testing for various analytes in a bodily fluid and yield results that are equivalent to laboratory testing. Although the devices are designed to be easy to use and reliable, the users of such devices commonly do not follow specific laboratory procedures, have extensive precision and accuracy double checks, and have control procedures. The meters/analyzers for such diagnostic tests must frequently be calibrated. This typically requires the waste of a test strip as well as the provision of calibration solution to dose the strip. The calibration solution may also degrade over time, therefore affecting the accuracy of the calibration.

BRIEF SUMMARY

In one embodiment, a system for calibrating an analyzer includes a test strip body. The system further includes a plurality of leads on the test strip body. The system further includes a circuit on the test strip body. The circuit includes a first resistor interconnected with at least a first portion of the plurality of leads and a second resistor interconnected with at least a second portion of the plurality of leads. When the test strip body is inserted into an analyzer, the circuit is configured to provide a signal simulating an electrochemical test strip. In one alternative, the first resistor is interconnected to the working electrode lead of the plurality of leads, wherein the working electrode lead when inserted into the analyzer provides an analyte signal to the analyzer, simulating the electrochemical test strip dosed with sample. In another alternative, the analyte signal is a constant resistance. Alternatively, the second resistor is interconnected to the fill electrode lead of the plurality of leads, wherein the fill electrode lead when inserted into the analyzer provides a fill resistance signal to the analyzer, simulating the electrochemical test strip dosed with sample. In another alternative, the fill resistance signal is a constant resistance In one embodiment, a system for calibrating an analyzer includes a test strip body. The system further includes a plurality of leads on the test strip body. The system further includes a circuit on the test strip body, the circuit including circuitry for simulating an electrochemical test strip when the test strip is inserted into an analyzer. Alternatively, the circuit includes a first resistor interconnected with at least a first portion of the plurality of leads and a second resistor interconnected with at least a second portion of the plurality of leads. In one alternative, the first resistor is interconnected to the working electrode lead of the plurality of leads, wherein the working electrode lead when inserted into the analyzer provides an analyte signal to the analyzer, simulating the electrochemical test strip dosed with sample and the second resistor is interconnected to the fill electrode lead of the plurality of leads, wherein the fill electrode lead when inserted into the analyzer provides a fill resistance signal to the analyzer, simulating the electrochemical test strip dosed with sample. Alternatively, the circuitry includes a plurality of electrical devices selected from a group consisting of resistors and capacitors. In another alternative, the circuitry includes a microprocessor. Alternatively, the microprocessor produces an analyte signal and a fill resistance signal. In another alternative, the analyte signal and the fill resistance signal are a constant resistance. Alternatively, the analyte signal and the fill resistance signal are a variable resistance. In another alternative, the microprocessor produces a signal voltage. Alternatively, the signal voltage is a constant voltage. In another alternative, the signal voltage is a variable voltage.

In one embodiment, a method of calibrating an analyzer includes providing a checkstrip. The checkstrip includes a test strip body. The checkstrip further includes a plurality of leads on the test strip body. The checkstrip further includes a circuit on the test strip body, the circuit including circuitry for simulating an electrochemical test strip when the test strip is inserted into an analyzer. The method further includes inserting the checkstrip into an analyzer and calibrating the analyzer with the checkstrip. Alternatively, the checkstrip includes a first resistor interconnected with at least a first portion of the plurality of leads and a second resistor interconnected with at least a second portion of the plurality of leads, the first resistor is interconnected to the working electrode lead of the plurality of leads. The working electrode lead when inserted into the analyzer provides an analyte signal to the analyzer, simulating the electrochemical test strip dosed with sample and the second resistor is interconnected to the fill electrode lead of the plurality of leads. The fill electrode lead when inserted into the analyzer provides a fill resistance signal to the analyzer, simulating the electrochemical test strip dosed with sample.

In one embodiment, a method of checking the circuitry of an analyzer includes providing a checkstrip. The checkstrip includes a test strip body. The checkstrip further includes a plurality of leads on the test strip body. The checkstrip further includes a circuit on the test strip body, the circuit including circuitry for simulating an electrochemical test strip when the test strip is inserted into an analyzer. The method further includes inserting the checkstrip into an analyzer and checking the circuitry the analyzer with the checkstrip. Alternatively, the checkstrip includes a first resistor interconnected with at least a first portion of the plurality of leads and a second resistor interconnected with at least a second portion of the plurality of leads, the first resistor is interconnected to the working electrode lead of the plurality of leads. The working electrode lead when inserted into the analyzer provides an analyte signal to the analyzer, simulating the electrochemical test strip dosed with sample and the second resistor is interconnected to the fill electrode lead of the plurality of leads. The fill electrode lead when inserted into the analyzer provides a fill resistance signal to the analyzer, simulating the electrochemical test strip dosed with sample.

DETAILED DESCRIPTION

Figure 1:
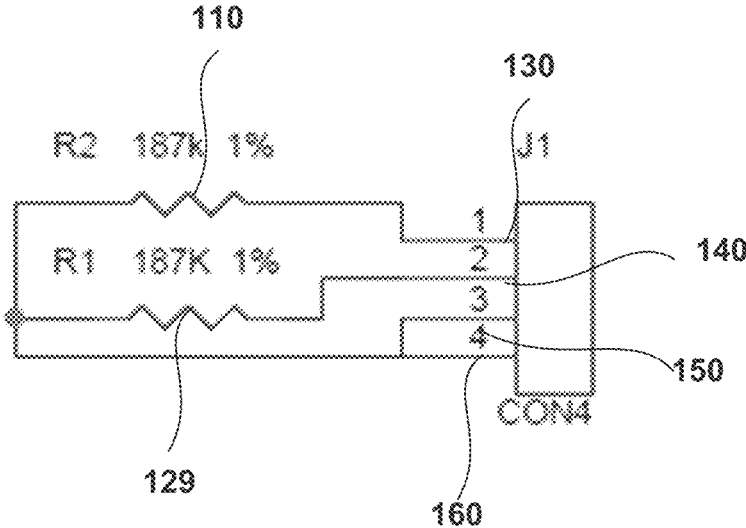
FIG. 1 shows one embodiment of circuitry for a simulated calibrator.

Certain terminology is used herein for convenience only and is not to be taken as a limitation on the embodiments of the systems and methods for a test strip calibrator simulating an electrochemical strip (simulated calibrator or Check-Strip). In many embodiments, the simulated calibrator includes a test strip body including the same electrochemical ports or leads used to connect the electrochemical strip to a meter/analyzer. However, instead of including a test area for receiving a sample and reacting the sample, the simulated calibrator includes resistors in order to simulate the resistance that would be provided by a dosed test strip, typically the dosed test strip dosed with a calibrator solution.

In many embodiments, the simulated calibrator is designed to determine if a meter's (or analyzer) port circuits are within a pre-determined electrical tolerance during manufacturing of meter (analyzer) and also during the operation of the analyzer prior to running controls and blood and for long term circuit aging of the analyzer to ensure that the system is operating as designed. In many embodiments, the test strip may be for testing for glucose or another analyte, such as A1c, lipids, etc. The subject matter herein is not specifically limited a particular analyte. Additionally, in alternatives, multiple test ports may be checked. In some embodiments, the simulated calibrator includes one or more resistors. In some embodiments, the simulated calibrator includes one or more capacitors. In some embodiments, the simulated calibrator includes one or more capacitors, resistors, and other circuitry designed to simulate a signal that an actual test strip would make when dosed with a sample. In some embodiments, a field-programmable gate array (FPGA) may be used in combination with other electrical components (resistors, etc.) to simulate the signal. In another embodiment, a microprocessor may be included to simulate a more complex signal. The microprocessor may be deployed with other electrical components including resistors, capacitors, etc. In some embodiments, the simulated calibrator may be used in simulating resistance (or other electrical characteristics) for a variety of different analyte/ test strip combinations. In this embodiment, the calibrator may have a selector, that enables selection of the calibration signal of interest. This may be accomplished via a microprocessor. Additionally, in this embodiment, the configurable simulated calibrator interacts with the meter, providing a signal to the meter that prompts the user to select the calibration signal of interest for the particular analyte test strip desired. In configurations where a simpler resistor/ capacitor system is used for the simulated calibrator, the meter may have no way of knowing that the simulated calibrator is not an actual test strip and may function according to the same protocol as normal. Alternatively, the simulated calibrator may be "smart" and may interact with the meter in such a way that the simulate calibrator is configurable.

In one embodiment, a simulated calibrator for an electrochemical glucose strip is provided. The simulated calibrator includes two pre-determined 187K Ohm resistors that will create a constant current in the test strip housing that will be measured by two Analog to Digital (A/D) converters in the meter in which the simulated calibrator is inserted. These measured A/D values are compared to values stored in electrically erasable programmable read-only memory (EEPROM) memory by software. A pass or fail will be determined in software if the A/D values are within the boundaries of the values in EEPROM memory. In alternatives, different type of memory may be used. An EEPROM memory is typically an insertable chip that provides calibrator data to a meter for a test strip that the EEPROM is associated with. The EEPROM may be test strip specific, as well as test strip lot specific.

With the simulated calibrator for glucose, the electrochemical test strip circuit can be tested by software of the meter to determine if the simulated calibrator circuit is functioning within acceptable limits with known resistor values. Given constant resistor values, software readings from the A/D converter values can then determine if the current values are within operating tolerances. These tolerances can be compared during manufacturing of the meter/ analyzer, during operation of the product and during electrochemical glucose strip aging of the product. A menu viewed by the tester can observe a Go/No Go indication that the electrochemical meter running the simulated calibrator is operating within pre-defined tolerances.

Prior to the simulated calibrator/CheckStrip, multi-chem liquid solutions are used with test strips to determine if the resultant measurements are within the range card of the multi-chem solution per a LOT of the multi-chem solution and a LOT of the test strips. The multi-chem solutions and test strips are disposable and must be resupplied and not re-usable. The multi-chem liquid solution and test strips typically have a shelf life. The simulated calibrator/Check-Strip can be reused hundreds to thousands of times as long as mechanically and electrically operable and shelf life of the simulated calibrator is far greater than the multi-chem solution and test strips.

The multi-chem results can vary from test to test with such multi-chem variability, test strip variability and sampling of the concentration depending on the fluid sense detection. The variability of the multi-chem solution and the variability of the test strips and sample timing is checked within a range of operation card for each LOT. The multi-chem solution is a solution that simulates a blood sample with glucose (or any other in it that is shelf stable and will produce a signal from an electrochemical signal). Using an CheckStrip, the resistance is constant from test to test and the resistance is constant in both the fluid sense circuit and the fluid measurement circuit and is independent of the sampling timing. (Comparing a level straight line versus comparing the shape of a curve and when the curve starts).

In many embodiments, the meter (or analyzer; throughout this disclosure, meter may be used interchangeably for analyzer) that the simulated calibrator mates with include software that provides for user interface systems. These systems may be menu based, GUI based, text based, or provide alternative interface systems. In some configurations, there is a visual menu operation Go/No Go for the CheckStrip.

The analyzer may also be configured to determine that the simulated calibrator is no longer in electrical tolerance from use or aging of the simulated calibrator. The analyzer can detect a Go/No Go from a simulated calibrator. In some embodiments, a new simulated calibrator can be used to determine if the analyzer is out of tolerance or the analyzer has detected a bad simulated calibrator and should be discarded. There is no mechanism using multi-chem solution and electrochemical test strips since they cannot be reused.

In many embodiments, the meter or analyzer is configured to require a MEMo Chip or similar system. The MEMo Chip provides calibration information for the lot (lot refers to the manufacturing lot of the test strip in this context and by be denoted as LOT) of electrochemical test strips used. Test strips may have different calibration information based on the specifics of the chemistry or other factors during their manufacturing. Typically, the test strips are used with their corresponding MEMo Chip that provides the lot specific calibration information. Typically, the lot numbers must match between chip and strip. Since the CheckStrip/simulated calibrator may be made to tighter electrical tolerances that have a high degree of reproducibility, a MEMo Chip or other calibration chip need not be used. This is because all CheckStrips may be manufactured such that electrically, they are significantly less than margins of error/tolerances. Resistors or other electrical components are reliably the same in function.

Furthermore, at times multi-Chem solution concentrations can change from LOT to LOT. Using the same eGlu Check Strip does not have this variability. Furthermore, multi-chem solutions may age and degrade over time, providing for reduced accuracy and performance, resulting in improper calibration.

In many embodiments, the meter or analyzer may have a GO/NO GO visual menu to detect that the simulated calibrator is inserted by using a microprocessor I/O pin and determine insertion or not insertion and can detect a bad connection.

FIG. 1 shows one embodiment of circuitry for a simulated calibrator. The simulated calibrator contains fixed resistors 110, 129 for the fluid sense (or fill electrode, in other words, an electrode when covered in fluid that indicates the presence of a sample up to the needed level for a proper test) and working electrode pins 1 and 2, 130, 140. The simulated calibrator is inserted to an analyzer/meter and pins 1 and 2, 130, 140 interact with the leads on the meter. Software resident in the analyzer will read the digital current from the A/D Converters using the circuit 100 in the CardioChek Plus analyzer. The simulated calibrator contains pins 3 and 4, 150, 160 that short the pins in the analyzer's port and the analyzer can detect that the strip detect circuitry is functional by reading an I/O port pin.

Figure 2:
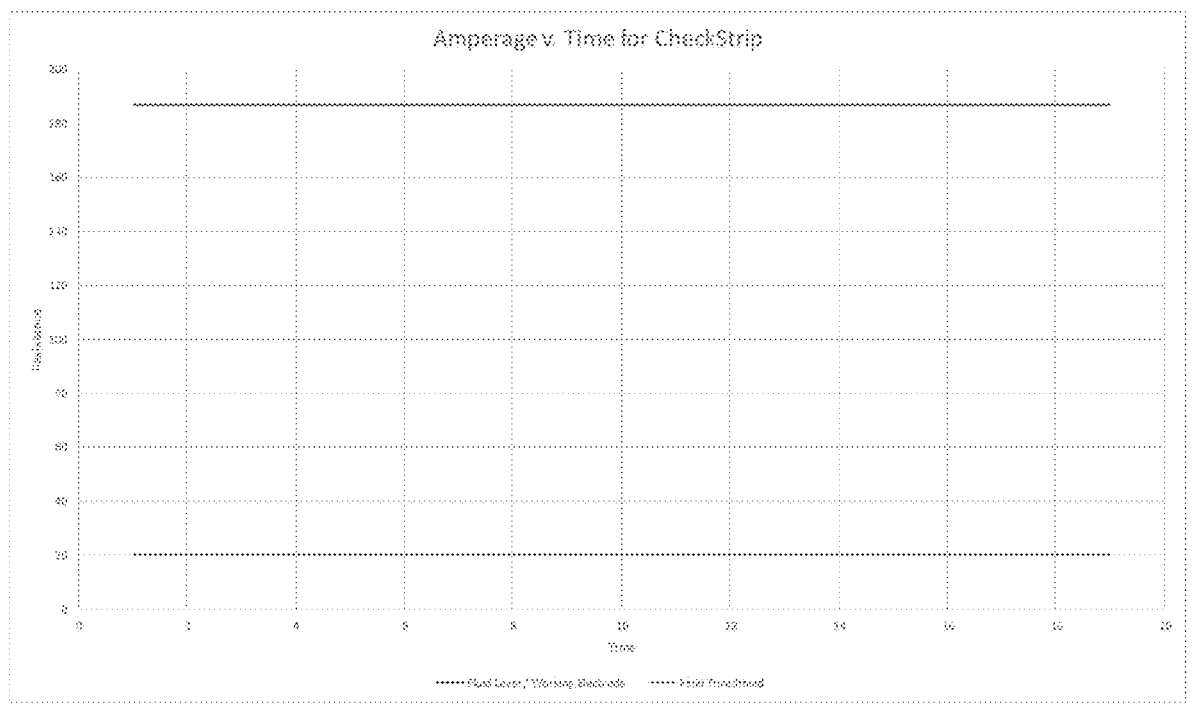
FIG. 2 shows an example of the current/resistance output of a simulated calibrator.

In FIG. 2, one A/D measures the current of the 187 k Ohm resister for the fluid sense pin. This is a constant nAmp reading per time. Another A/D measures the current of the 187 kOhm resister for the working electrode/fill electrode pin. This is also a constant reading per time. These readings are consistent from test to test and from analyzer to analyzer. These readings are compared to a tolerance window stored in EEPROM to be used for a Go/No Go for each test.

Figure 3:
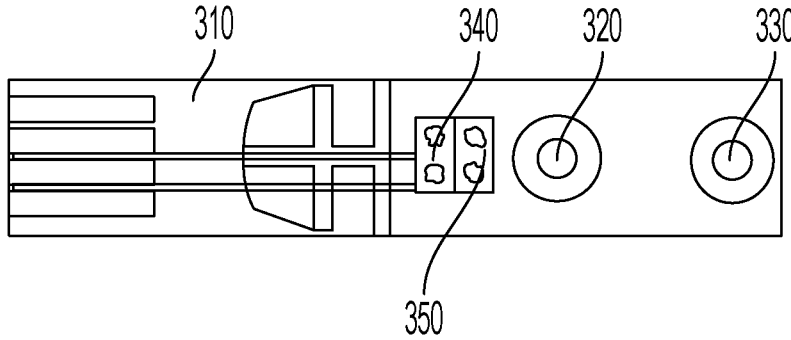
FIG. 3 shows one embodiment of a test strip for a simulated calibrator.

FIG. 3 shows one embodiment of a printed circuit board 310 with holes 320, 330 for the handle, resistors 340, 350 in place and connector to insert into the analyzer. In some embodiments, resistors 340, 350 may be replaced with microprocessors. In some embodiments, resistors 340, 350 may be replaced with other circuitry, such as capacitors, resistors, and some combination thereof. In some embodiments, constant current is provided by the simulated calibrator. In some embodiments, variable current is provided by the simulated calibrator. In some embodiments, constant voltage is provided by the simulated calibrator. In some embodiments, constant voltage is provided by the simulated calibrator.

In some embodiments, the meter software may be completely unchanged and still function properly with a simulated calibrator. In other embodiments, the meter/analyzer software may be modified to provide for enhanced interaction with the meter/analyzer. Enhanced operations may include special operations for selecting the calibration of the meter or a check of the wear of the circuitry of the meter.

In many embodiments, parts of the system are provided in devices including microprocessors. Various embodiments of the systems and methods described herein may be implemented fully or partially in software and/or firmware. This software and/or firmware may take the form of instructions contained in or on a non-transitory computer-readable storage medium. Those instructions then may be read and executed by one or more processors to enable performance of the operations described herein. The instructions may be in any suitable form such as, but not limited to, source code, compiled code, interpreted code, executable code, static code, dynamic code, and the like. Such a computer-readable medium may include any tangible non-transitory medium for storing information in a form readable by one or more computers such as, but not limited to, read only memory (ROM); random access memory (RAM); magnetic disk storage media; optical storage media; a flash memory, etc.

Embodiments of the systems and methods described herein may be implemented in a variety of systems including, but not limited to, smartphones, tablets, laptops, and combinations of computing devices and cloud computing resources. For instance, portions of the operations may occur in one device, and other operations may occur at a remote location, such as a remote server or servers. For instance, the collection of the data may occur at a smartphone, and the data analysis may occur at a server or in a cloud computing resource. Any single computing device or combination of computing devices may execute the methods described.

In various instances, parts of the method may be implemented in modules, subroutines, or other computing structures. In many embodiments, the method and software embodying the method may be recorded on a fixed tangible medium.

While specific embodiments have been described in detail in the foregoing detailed description, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein but is intended to cover modifications within the spirit and scope thereof as defined by the appended claims and any and all equivalents thereof.

What is claimed as new and desired to be protected by Letters Patent of the United States is:

1. A system for calibrating an analyzer, the system comprising:
    a test strip body;
    a plurality of leads on the test strip body;
    a circuit on the test strip body, the circuit including:
        a first resistor directly interconnected with at least a first portion of the plurality of leads;
        a second resistor directly interconnected with at least a second portion of the plurality of leads; and
        an analyzer, the test strip body removable and insertable into the analyzer, the analyzer configured to execute a software to determine whether port circuits of the analyzer that interface with leads of the plurality of leads for a working electrode and a reference electrode are out of electrical tolerance with the test strip body coupled to the analyzer;
    wherein, when the test strip body is inserted into the analyzer, the circuit is configured to provide a signal simulating an electrochemical test strip through the same leads the circuit would stimulate and the analyzer mates with the circuit and executes the software that displays a user interface on the analyzer and determines whether the port circuits of the analyzer are out of electrical tolerance.

2. The system of claim 1, wherein the first resistor is interconnected to a working electrode lead of the plurality of leads, wherein the working electrode lead when inserted into the analyzer provides an analyte signal to the analyzer, simulating the electrochemical test strip dosed with sample.

3. The system of claim 2, wherein the analyte signal is a constant resistance.

4. The system of claim 1, wherein the second resistor is interconnected to a fill electrode lead of the plurality of leads, wherein the fill electrode lead when inserted into the analyzer provides a fill resistance signal to the analyzer, simulating the electrochemical test strip dosed with sample.

5. The system of claim 4, wherein the fill resistance signal is a constant resistance.

6. A system for calibrating an analyzer, the system comprising:

a test strip body;

a plurality of leads on the test strip body;

an analyzer, the test strip body removable and insertable into the analyzer, the analyzer configured to execute a software to determine whether port circuits of the analyzer that interface with leads for a working electrode and a reference electrode are out of electrical tolerance with the test strip body coupled to the analyzer, the analyzer displaying an indication that the analyzer is out of tolerance when determined; and a circuit on the test strip body, the circuit including circuitry for simulating an electrochemical test strip when the test strip body is inserted into the analyzer and the analyzer mates with the circuit and executes the software that displays a user interface on the analyzer and determines whether the port circuits of the analyzer are out of electrical tolerance, wherein the circuitry includes a first resistor directly interconnected with a least a first portion of the plurality of leads; and a second resistor directly interconnected with at least a second portion of the plurality of leads.

7. The system of claim 6, wherein the first resistor is interconnected to a working electrode lead of the plurality of leads, wherein the working electrode lead when inserted into the analyzer provides an analyte signal to the analyzer, simulating the electrochemical test strip dosed with sample and the second resistor is interconnected to a fill electrode lead of the plurality of leads, wherein the fill electrode lead when inserted into the analyzer provides a fill resistance signal to the analyzer, simulating the electrochemical test strip dosed with sample.

8. The system of claim 6, wherein the circuitry includes a plurality of electrical devices selected from a group consisting of resistors and capacitors.

* * * * *